(12) United States Patent
Suty-Heinze et al.

(10) Patent No.: US 8,044,036 B2
(45) Date of Patent: Oct. 25, 2011

(54) FUNGICIDAL ACTIVE INGREDIENT COMBINATION

(75) Inventors: Anne Suty-Heinze, Langenfeld (DE); Burkhard Schütz, Düsseldorf (DE)

(73) Assignee: Bayer Cropscience AG, Monheim (DE)

(*) Notice: Subject to any disclaimer, the term of this patent is extended or adjusted under 35 U.S.C. 154(b) by 633 days.

(21) Appl. No.: 11/914,704

(22) PCT Filed: May 24, 2006

(86) PCT No.: PCT/EP2006/004930
§ 371 (c)(1),
(2), (4) Date: Jun. 11, 2008

(87) PCT Pub. No.: WO2006/125618
PCT Pub. Date: Nov. 30, 2006

(65) Prior Publication Data
US 2009/0069178 A1    Mar. 12, 2009

(30) Foreign Application Priority Data
May 24, 2005   (DE) .................... 10 2005 023 835

(51) Int. Cl.
*A01N 55/10* (2006.01)
*A01N 43/10* (2006.01)
*A01N 43/653* (2006.01)
(52) U.S. Cl. ............ 514/63; 514/384; 514/448; 504/100
(58) Field of Classification Search .................... 514/63, 514/384, 448; 504/100
See application file for complete search history.

(56) References Cited

U.S. PATENT DOCUMENTS

| | | | |
|---|---|---|---|
| 5,599,828 A | 2/1997 | Zeun et al. | |
| 5,859,039 A | 1/1999 | Jautelat et al. | |
| 5,998,455 A | 12/1999 | Knauf-Beiter et al. | |
| 6,306,850 B1 | 10/2001 | Dutzmann et al. | |
| 6,355,634 B1 | 3/2002 | Isenring et al. | |
| 6,407,100 B1 | 6/2002 | Isenring et al. | |
| 6,602,823 B1 | 8/2003 | Röchling et al. | |
| 7,655,599 B2 | 2/2010 | Rochling et al. | |
| 2005/0101639 A1 | 5/2005 | Ammermann et al. | |
| 2005/0165076 A1 | 7/2005 | Ammermann et al. | |
| 2006/0004070 A1 | 1/2006 | Wachendorff-Neumann et al. | |
| 2006/0014738 A1 | 1/2006 | Wachendorff-Neumann et al. | |
| 2006/0035942 A1 | 2/2006 | Wachendorff-Neumann et al. | |
| 2007/0037799 A1 | 2/2007 | Dahmen et al. | |
| 2007/0054804 A1 | 3/2007 | Suty-Heinze | |
| 2007/0060579 A1 | 3/2007 | Wachendorff-Neumann et al. | |
| 2007/0155706 A1* | 7/2007 | Andersch et al. ............. | 514/114 |
| 2007/0293550 A1 | 12/2007 | Rochling et al. | |
| 2007/0298966 A1 | 12/2007 | Fischer et al. | |
| 2008/0113864 A1 | 5/2008 | Grosser et al. | |
| 2008/0139389 A1 | 6/2008 | Kneen et al. | |
| 2008/0269051 A1 | 10/2008 | Suty-Heinze et al. | |
| 2008/0269263 A1 | 10/2008 | Dahmen et al. | |
| 2009/0170918 A1 | 7/2009 | Wolf | |
| 2009/0286681 A1 | 11/2009 | Dahmen et al. | |
| 2011/0009267 A1 | 1/2011 | Suty-Heinze | |
| 2011/0033433 A1 | 2/2011 | Davies et al. | |
| 2011/0034496 A1 | 2/2011 | Häuser-Hahn et al. | |
| 2011/0064827 A1 | 3/2011 | Seitz et al. | |

FOREIGN PATENT DOCUMENTS

| | | |
|---|---|---|
| GB | 2 262 037 A | 6/1993 |
| WO | WO 96/16048 A1 | 5/1996 |
| WO | WO 96/18631 A1 | 6/1996 |
| WO | WO 98/47367 A1 | 10/1998 |
| WO | WO 00/63188 A1 | 10/2000 |
| WO | WO 2004/095929 | * 11/2004 |
| WO | WO 2009/124707 | 10/2009 |

OTHER PUBLICATIONS

International Search Report for International Application No. PCT/EP2006/004930, European Patent Office, Netherlands, mailed on Aug. 30, 2006.
Bauer, T.A., et al., "Response of Selected Weed Species to Postemergence Imazethapyr and Bentazon," *Weed Tech*. 9:236-242, The Weed Science Society of America (1995).
Blackshaw, R.E., "HOE-39866 Use in Chemical Fallow Systems," *Weed Tech*. 3:420-428, The Weed Science Society of America (1989)
Blackshaw, R.E., "Synergistic Mixes of DPX-A7881 and Clopyralid in Canola (Brassica napus)," Weed Tech. 3:690-695, The Weed Science Society of America (1989).
Blackshaw, R.E., "Syneergistic Mixes of DPX-A7881 and Clopyralid in Canola (*Brassica napus*)," *Weed Tech*. 3:690-695, The Weed Science Society of America (1989).
Blackshaw, R.E., et al., "Herbicide Combinations for Postemergent Weed Control in Safflower (*Carthamus tinctorius*)," *Weed Tech*. 4:97-104, The Weed Science Society of America (1990).
Blouin, D.C., et al., "Analysis of Synergistic and Antagonistic Effects of Herbicides NPL6 Using Nonlinear Mixed-Model Methodology," *Weed Tech* 18:464-472, The Weed Science Society of America (2004).

(Continued)

*Primary Examiner* — John Pak
(74) *Attorney, Agent, or Firm* — Sterne, Kessler, Goldstein & Fox P.L.L.C.

(57) ABSTRACT

An active-compound combination of (prothioconazole) and (silthiofam)

has very good fungicidal properties.

10 Claims, No Drawings

OTHER PUBLICATIONS

Bradley, P.R., et al., "Response of Sorghum (*Sorghum bicolor*) to Atrazine, NPL7 Ammonium Sulfate, and Glyphosate," *Weed Tech.* 14:15-18, The Weed Science Society of America (2000).

Buker, III, R.S., et al., "Confirmation and Control of a Paraquat-Tolerant Goosegrass NPL8 (*Eleusine indica*) Biotype," *Weed Tech.* 16:309-313, The Weed Science Society of America (2002).

Burke, I.C., et al., "CGA-362622 Antagonizes Annual Grass Control with Clethodim," *Weed Tech.* 16:749-754, The Weed Science Society of America (2002).

Colby, S.R., "Calculating Synergistic and Antagonistic Responses of Herbicide Combinations," *Weeds* 15:20-22, Weed Society of America (1967).

Flint, J.L., et al., "Analyzing Herbicide Interactions, A Statistical Treatment of Colby's Method," *Weed Tech.* 2:304-309, The Weed Science Society of America (1988).

Gillespie, G.R., and Nalewaja, J.D., "Wheat (*Triticum aestivum*) Response to Triallate Plus Chlorsulfuron," *Weed Tech.* 3:20-23, The Weed Science Society of America (1989).

Green, J.M., et aL, "Metribuzin and Chlorimuron Mixtures for Preemergence.Broadleaf Weed Control in Soybeans, *Glycine max*," *Weed Tech.* 2:355-363, The Weed Science Society of America (1988).

Harker, K.N., and O'Sullivan, P.A., "Synergistic Mixtures of Sethoxydim and Fluazifop on Annual Grass Weeds," *Weed Tech.* 5:310-316, The Weed Science Society of America (1991).

Kent, L.M., et al., "Effect of Ammonium Sulfate, Imazapyr, and Environment on the Phytotoxicity of Imazethapyr," *Weed Tech.* 5:202-205, The Weed Science Society of America (1991).

Kotoula-Syka, E., et al., "Interactions between San 582H and Selected Safeners on Grain Sorghum (*Sorghum bicolor*) and Corn (*Zea mays*)," *Weed Tech.* 10:299-304, The Weed Science Society of America (1996).

Lanclos, D.Y., et al., "Glufosinate Tank-Mix Combinations in Glufosinate-Resistant Rice (*Oryza sativa*)," *Weed Tech.* 16:659-663, The Weed Science Society of America (2002).

Norris, J.L., et al., "Weed Control from Herbicide Combinations with Three Formulations of Glyphosate," *Weed Tech.* 15:552-558, The Weed Science Society of America (2001).

Novosel, K.M. et al., "Metolachlor Efficacy as Influenced by Three Acetolactate Synthase-Inhibiting Herbicides," *Weed Tech.* 12:248-253, The Weed Science Society of America (1998).

Palmer, E.W. et al., "Broadleaf Weed Control in Soybean (*Glycine max*) with CGA-277476 and Four Postemergence Herbicides," *Weed Tech.* 14:617-623, The Weed Science Society of American (2000).

Rummens, F.H.A., "An Improved Definition of Synergistic and Antagonistic Effects," *Weed Science* 23(I):4-6, The Weed Science Society of America, United States (1975).

Salzman, F.P., and Renner, K.A., "Response of Soybean to Combinations of Clomazone, Metribuzin, Linuron, Alachlor, and Atrazine," *Weed Tech.* 6:922-929, The Weed Science Society of Ameria (1992).

Scott, R.C., et al., "Spray Adjuvant, Formulation, and Environmental Effects on Synergism from Post-Applied Tank Mixtures of San 582H with Fluazifop-P, Imazethapyr, and Sethoxydim," *Weed Tech.* 12:463-469, The Weed Science Society of America (1998).

Shaw, D.R. And Arnold, J.C., "Weed Control from Herbicide Combinations with Glyphosate," *Weed Tech.* 16:1-6, The Weed Science Society of America (2002).

Snipes, C.E., and Allen, R.L., "Interaction of Graminicides Applied in Combination with Pyrithiobac," *Weed Tech.* 10:889-892, The Weed Science Society of America (1996).

Sun, Y.-P. & Johnson, E.R., "Analysis of Joint Action of Insecticides Against House Flies", *J. Econ. Entomol.* 53:887-892, United States (1960).

Tammes, P.M.L., "Isoboles, A Graphic Representation of Synergism in Pesticides," *Neth. J. Plant Path.* 70:73-80, Springer, Germany (1964).

Tomlin, C., ed., *The Pesticide Manual*, Eleventh Edition, 1242-1245, British Crop Protection Council, Farnham, UK (1997).

Wehtje, G. And Walker, R.H., "Interaction of Glyphosate and 2,4-DB for the Control of Selected Morningglory (*Ipomoea* spp.) Species," *Weed Tech.* 11:152-156, The Weed Science Society of America (1997).

Zhang, W., et al., "Fenoxaprop Interactions for Barnyardgrass (*Echinochloa crus-galli*) Control in Rice," *Weed Tech.* 19:293-297, The Weed Science Society of America (2005).

Opposition Proceeding in European Patent No. EP-B-1482798, Mar. 5, 2007-Nov. 9, 2009 , with partial English translation.

Prosecution History of European Patent Appl. No. 03735610.2 (Euroepan counterpart of U.S. Appl. No. 10/518,742), Jul. 13, 2006-Sep. 25, 2009, with partial English translation.

Partial English language translation of Prosecution History of European Patent Appl. No. 03735610.2, Jul. 13, 2006-Sep. 25, 2009.

Partial English language translation of Opposition Proceeding in European Patent No. EP-B-1482798, Feb. 26, 2007-Nov. 9, 2009.

"Azoxystrobin data sheet," Compendium of Pesticide Common Names, accessed at http://www.alanwood.net/pesticides/azoxystrobin.html, accessed on Apr. 8, 2009, 1 page.

"Kresoxim-methyl data sheet," Compendium of Pesticide Common Names, accessed at http://www.alanwood.net/pesticides/lcresoxim-methyl.html, accessed on Apr. 8, 2009, 1 page.

"Metominostrobin data sheet," Compendium of Pesticide Common Names, accessed at http://www.alanwood.net/pesticides/metominostrobin.html, accessed on Apr. 8, 2009, 1 page.

* cited by examiner

FUNGICIDAL ACTIVE INGREDIENT COMBINATION

This application is a US National Stage of International Application No. PCT/EP2006/004930, filed May 24, 2006, which claims the benefit of German Patent Application No. 10 2005 023835.1, filed May 24, 2005. The entirety of each of these applications is incorporated by reference herein.

The invention relates to an active-compound combination comprising the known active compound prothioconazole, which combination is highly suitable for controlling phytopathogenic fungi.

It is already known that prothioconazole has very good fungicidal properties.

However, since the ecological and economical demands made on modern fungicides are increasing constantly, for example with respect to activity spectrum, toxicity, selectivity, application rate, formation of residues and favourable manufacture, and there can furthermore be problems, for example, with resistance, there is a constant need to develop novel fungicides which, at least in some areas, have advantages over those of the prior art.

Surprisingly, it has now been found that a combination of prothioconazole with the known fungicidally active compound silthiofam is highly suitable for controlling phytopathogenic fungi—in particular by seed dressing.

Accordingly, the invention provides an active-compound combination, comprising the compound of the formula (I)

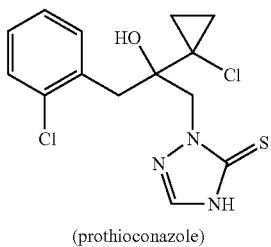

(prothioconazole)

and the compound of the formula (II)

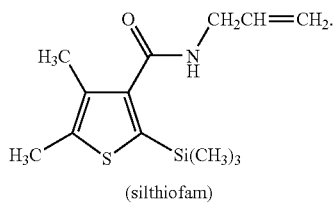

(silthiofam)

Surprisingly, the fungicidal activity of the active-compound combination according to the invention is considerably higher than the sum of the activities of the individual active compounds. Thus, an unforeseeable true synergistic effect is present, and not just an addition of activities.

Prothioconazole (IUPAC name: 2-[(2RS)-2-(1-chlorocyclopropyl)-3-(2-chlorophenyl)-2-hydroxy-propyl]-2H-1,2, 4-triazole-3(4H)thione) is known from WO-A 96/16048. Data for reference and properties can be found, for example, in C. D. S. Tomlin, The Pesticide Manual, 13th ed., The British Crop Protection Council, Farnham 2003.

The compound of the formula (I) is shown in the "thieno" form which is in a steady state with the tautomeric mercapto form:

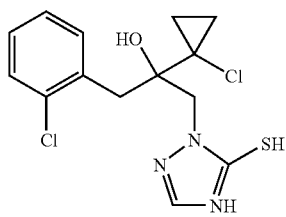

For the sake of simplicity, hereinbelow only the thieno form is shown.

In addition to the racemic form of the compound (I), preferred use is also made of the (−)-enantiomer (known from WO-A 00/63188) and the thermodynamically stable crystal form II (known from PCT/EP 03/07433).

Mixtures of prothioconazole with further fungicides are described, for example, in WO-A 98/47367.

Silthiofam (IUPAC name N-alkyl-4,5-dimethyl-2-(trimethylsilyl)thiophene-3-carboxamide) is known, for example, from EP-A 0 538 231. Statements on references and properties can be found, for example, in The Pesticide Manual, 13th ed., The British Crop Protection Council, Farnham 2003.

The synergistic effect is particularly pronounced when the active compounds in the active-compound combination according to the invention are present in certain weight ratios. However, the weight ratios of the active compounds in the active-compound combination can be varied within a relatively wide range.

In general, 0.02-20 parts by weight, preferably 0.05-10 parts by weight, of active compound of the formula (II) are present per part by weight of the active compound of the formula (I).

The active-compound combination according to the invention has potent microbicidal activity and can be employed for controlling unwanted microorganisms, such as fungi and bacteria, in crop protection and in the protection of materials.

Fungicides can be employed in crop protection for example for controlling Plasmodiophoromycetes, Oomycetes, Chytridiomycetes, Zygomycetes, Ascomycetes, Basidiomycetes and Deuteromycetes.

Bactericides can be employed in crop protection for example for controlling Pseudomonadaceae, Rhizobiaceae, Enterobacteriaceae, Corynebacteriaceae and Streptomycetaceae.

Some pathogens which cause fungal and bacterial diseases and come under the generic names listed above may be mentioned by way of example but not of limitation:

*Xanthomonas* species, such as, for example, *Xanthomonas campestris* pv. *oryzae*;
*Pseudomonas* species, such as, for example, *Pseudomonas syringae* pv. *lachrymans*;
*Erwinia* species, such as, for example, *Erwinia amylovora*;
*Pythium* species, such as, for example, *Pythium ultimum*;
*Phytophthora* species, such as, for example, *Phytophthora infestans*;
*Pseudoperonospora* species, such as, for example, *Pseudoperonospora humuli* or *Pseudoperonospora cubensis*;
*Plasmopara* species, such as, for example, *Plasmopara viticola*;
*Bremia* species, such as, for example, *Bremia lactucae*;
*Peronospora* species, such as, for example, *Peronospora pisi* or *P. brassicae*;
*Erysiphe* species, such as, for example, *Erysiphe graminis*;
*Sphaerotheca* species, such as, for example, *Sphaerotheca fuliginea*;

*Podosphaera* species, such as, for example, *Podosphaera leucotricha*;
*Venturia* species, such as, for example, *Venturia inaequalis*;
*Pyrenophora* species, such as, for example, *Pyrenophora teres* or *P. graminea*
(conidia form: *Drechslera*, syn: *Helminthosporium*);
*Cochliobolus* species, such as, for example, *Cochliobolus sativus*
(conidia form: *Drechslera*, syn: *Helminthosporium*);
*Uromyces* species, such as, for example, *Uromyces appendiculatus*;
*Puccinia* species, such as, for example, *Puccinia recondita*;
*Sclerotinia* species, such as, for example, *Sclerotinia sclerotiorum*;
*Tilletia* species, such as, for example, *Tilletia caries*;
*Ustilago* species, such as, for example, *Ustilago nuda* or *Ustilago avenae*;
*Pellicularia* species, such as, for example, *Pellicularia sasakii*;
*Pyricularia* species, such as, for example, *Pyricularia oryzae*;
*Fusarium* species, such as, for example, *Fusarium culmorum*;
*Botrytis* species, such as, for example, *Botrytis cinerea*;
*Septoria* species, such as, for example, *Septoria nodorum*;
*Leptosphaeria* species, such as, for example, *Leptosphaeria nodorum*;
*Cercospora* species, such as, for example, *Cercospora canescens*;
*Alternaria* species, such as, for example, *Alternaria brassicae*;
*Pseudocercosporella* species, such as, for example, *Pseudocercosporella herpotrichoides*;
*Phakopsora* species, such as *Phakopsora pachyrhizi* and *Phakopsora meibomiae*; and
*Rhizoctonia* species, such as, for example, *Rhizoctonia solani*.

The active compounds according to the invention also show a strong invigorating action in plants. Accordingly they are suitable for mobilizing the internal defences of the plant against attack by unwanted microorganisms.

In the present context, plant-invigorating (resistance-inducing) compounds are to be understood as meaning substances which are capable of stimulating the defence system of plants such that, when the treated plants are subsequently inoculated with unwanted microorganisms, they display substantial resistance to these microorganisms.

In the present case, unwanted microorganisms are to be understood as meaning phytopathogenic fungi and bacteria. The compounds according to the invention can thus be used to protect plants within a certain period of time after treatment against attack by the pathogens mentioned. The period of time for which this protection is achieved generally extends for 1 to 10 days, preferably 1 to 7 days, from the treatment of the plants with the active compounds.

The active-compound combination of the invention is particularly suitable for controlling cereal diseases, such as *Cochliobolus, Pyrenophora, Fusarium, Tilletia, Ustilago, Rhizoctonia, Erysiphe, Ophiobolus, Pyrenophora, Rhynchosporium, Septoria, Pseudocercosporella* and *Leptosphaeria*.

The fact that the active-compound combination is well tolerated by plants at the concentrations required for controlling plant diseases permits the treatment of above-ground parts of plants, of propagation stock and seeds, and of the soil. The active-compound combination of the invention can be used for foliar application or else as seed dressing.

Accordingly, the invention also provides seed, coated with the active-compound combination according to the invention.

The active-compound combination according to the invention is also suitable for increasing the yield of crops. In addition, it shows reduced toxicity and is well tolerated by plants.

According to the invention, it is possible to treat all plants and parts of plants. Plants are to be understood here as meaning all plants and plant populations, such as desired and undesired wild plants or crop plants (including naturally occurring crop plants). Crop plants can be plants which can be obtained by conventional breeding and optimization methods or by biotechnological and genetic engineering methods or combinations of these methods, including the transgenic plants and including plant cultivars which can or cannot be protected by varietal property rights. Parts of plants are to be understood as meaning all above-ground and below-ground parts and organs of plants, such as shoot, leaf, flower and root, examples which may be mentioned being leaves, needles, stems, trunks, flowers, fruit-bodies, fruits and seeds and also roots, tubers and rhizomes. Parts of plants also include harvested material and vegetative and generative propagation material, for example seedlings, tubers, rhizomes, cuttings and seeds.

As already mentioned above, it is possible to treat all plants and their parts according to the invention. In a preferred embodiment, wild plant species and plant cultivars, or those obtained by conventional biological breeding methods, such as crossing or protoplast fusion, and parts thereof, are treated. In a further preferred embodiment, transgenic plants and plant cultivars obtained by genetic engineering methods, if appropriate in combination with conventional methods (genetically modified organisms), and parts thereof, are treated. The term "parts" or "parts of plants" or "plant parts" has been explained above.

With particular preference, plants of the plant cultivars which are in each case commercially available or in use are treated according to the invention. Plant cultivars are to be understood as meaning plants having new properties (traits) and which have been obtained by conventional breeding, by mutagenesis or by recombinant DNA techniques. They can be cultivars, biotypes or genotypes.

Depending on the plant species or plant cultivars, their location and growth conditions (soils, climate, vegetation period, diet), the treatment according to the invention may also result in superadditive (synergistic) effects. Thus, for example, reduced application rates and/or a widening of the activity spectrum and/or an increase in the activity of the substances and compositions which can be used according to the invention, better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products are possible which exceed the effects which were actually to be expected.

The transgenic plants or plant cultivars (i.e. those obtained by genetic engineering) which are preferably to be treated according to the invention include all plants which, in the genetic modification, received genetic material which imparted particularly advantageous useful properties (traits) to these plants. Examples of such properties are better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products. Further and particularly emphasized examples of such properties are a better defence of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), maize, soya beans, potatoes, cotton, oilseed rape and also fruit plants (with the fruits apples, pears, citrus fruits and grapes), and particular emphasis is given to maize, soya beans, potatoes, cotton and oilseed rape. Traits that are emphasized are in particular increased defence of the plants against insects by toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c, Cry2Ab, Cry3Bb and CryIF and also combinations thereof) (hereinbelow referred to as "Bt plants"). Traits that are also particularly emphasized are the increased defence of the plants against fungi, bacteria and viruses by systemic acquired resistance (SAR), systemin, phytoalexins, elicitors and resistance genes and correspondingly expressed proteins and toxins. Traits that are furthermore particularly emphasized are the increased tolerance of the plants to certain herbicidally active compounds, for example imidazolinones, sulphonylureas, glyphosate or phosphinotricin (for example the "PAT" gene). The genes which impart the desired traits in question can also be present in combination with one another in the transgenic plants. Examples of "Bt plants" which may be mentioned are maize varieties, cotton varieties, soya bean varieties and potato varieties which are sold under the trade names YIELD GARD® (for example maize, cotton, soya beans), KnockOut® (for example maize), StarLink® (for example maize), Bollgard® (cotton), Nucotn® (cotton) and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya bean), Liberty Link® (tolerance to phosphinotricin, for example oilseed rape), IMI® (tolerance to imidazolinones) and STS® (tolerance to sulphonylureas, for example maize). Herbicide-resistant plants (plants bred in a conventional manner for herbicide tolerance) which may be mentioned also include the varieties sold under the name Clearfield® (for example maize). Of course, these statements also apply to plant cultivars which have these genetic traits or genetic traits still to be developed and which will be developed and/or marketed in the future.

The plants listed can be treated according to the invention in a particularly advantageous manner with the active-compound mixtures according to the invention. The preferred ranges stated above for the active compounds or mixtures also apply to the treatment of these plants. Particular emphasis is given to the treatment of plants with the mixtures specifically mentioned in the present text.

The treatment of the plants and parts of plants according to the invention with the active compounds is carried out directly or by action on their environment, habitat or storage area according to customary treatment methods, for example by dipping, spraying, evaporating, atomizing, broadcasting, brushing-on and, in the case of propagation material, in particular in the case of seeds, further by single- or multi-layer coating.

The active-compound combination according to the invention can be converted into the customary formulations, such as solutions, emulsions, suspensions, powders, foams, pastes, granules, aerosols and microencapsulations in polymeric substances and in coating compositions for seeds, and ULV formulations.

These formulations are produced in a known manner, for example by mixing the active compounds or the active-compound combinations with extenders, that is, liquid solvents, pressurized liquefied gases and/or solid carriers, optionally with the use of surface-active agents, that is emulsifers and/or dispersants, and/or foam formers. If the extender used is water, it is also possible to employ for example organic solvents as cosolvents. Suitable liquid solvents are essentially: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, and also water. Liquefied gaseous extenders or carriers are those liquids which are gaseous at ambient temperature and at atmospheric pressure, for example aerosol propellants such as butane, propane, nitrogen and carbon dioxide. As solid carriers there are suitable: for example ground natural minerals, such as kaolins, clays, talc, chalk, quartz, attapulgite, montmorillonite or diatomaceous earth, and ground synthetic minerals, such as finely divided silica, alumina and silicates. As solid carriers for granules there are suitable: for example crushed and fractionated natural rocks such as calcite, pumice, marble, sepiolite and dolomite, and also synthetic granules of inorganic and organic meals, and granules of organic material such as sawdust, coconut shells, maize cobs and tobacco stalks. As emulsifiers and/or foam formers there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and protein hydrolysates. As dispersants there are suitable: for example lignin-sulphite waste liquors and methylcellulose.

Tackifiers such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other possible additives are mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95% by weight of active compound, preferably between 0.5 and 90%.

The active-compound combination according to the invention, as such or in its formulations, can also be used as a mixture with known fungicides, bactericides, acaricides, nematicides or insecticides, for example, to improve the activity spectrum or prevent the development of resistance. In many instances, synergistic effects are obtained, i.e. the activity of the mixture exceeds the activity of the individual components.

A mixture with other known active compounds, such as herbicides, safeners and/or semiochemicals or with fertilizers and growth regulators is also possible.

Examples of co-components in mixtures are the following compounds

Fungicides:
1) Nucleic acid synthesis inhibitors: for example benalaxyl, benalaxyl-M, bupirimate, clozylacon, dimethirimol, ethirimol, furalaxyl, hymexazol, mefenoxam, metalaxyl, metalaxyl-M, ofurace, oxadixyl, oxolinic acid;
2) mitosis and cell division inhibitors: for example benomyl, carbendazim, diethofencarb, ethaboxam, fuberidazole, pencycuron, thiabendazole, thiophanate-methyl, zoxamide;
3) respiration inhibitors (inhibitors of the respiratory chain):
3.1) inhibitors which act on complex I of the respiratory chain: for example diflumetorim;
3.2) inhibitors which act on complex II of the respiratory chain: for example boscalid/nicobifen, carboxin, fenfuram, flutolanil, furametpyr, furmecyclox, mepronil, oxycarboxin, penthiopyrad, thifluzamide;
3.3) inhibitors which act on complex III of the respiratory chain: for example amisulbrom, azoxystrobin, cyazofamid, dimoxystrobin, enestrobin, famoxadone, fenamidone, fluoxastrobin, kresoxim-methyl, metominostrobin, orysastrobin, picoxystrobin, pyraclostrobin, trifloxystrobin;
4) decouplers: for example dinocap, fluazinam, meptyldinocap;
5) ATP production inhibitors: for example fentin acetate, fentin chloride, fentin hydroxide, silthiofam;
6) amino acid and protein biosynthesis inhibitors: for example andoprim, blasticidin-S, cyprodinil, kasugamycin, kasugamycin hydrochloride hydrate, mepanipyrim, pyrimethanil;
7) signal transduction inhibitors: for example fenpiclonil, fludioxonil, quinoxyfen;
8) lipid and membrane synthesis inhibitors: for example biphenyl, chlozolinate, edifenphos, iodocarb, iprobenfos, iprodione, isoprothiolane, procymidone, propamocarb, propamocarb hydrochloride, pyrazophos, tolclofos-methyl, vinclozolin;
9) inhibitors of ergosterol biosynthesis: for example aldimorph, azaconazole, bitertanol, bromuconazole, cyproconazole, diclobutrazole, difenoconazole, diniconazole, diniconazole-M, dodemorph, dodemorph acetate, epoxiconazole, etaconazole, fenarimol, fenbuconazole, fenhexamid, fenpropidin, fenpropimorph, fluquinconazole, flurprimidol, flusilazole, flutriafol, furconazole, furconazole-cis, hexaconazole, imazalil, imazalil sulphate, imibenconazole, ipconazole, metconazole, myclobutanil, naftifine, nuarimol, oxpoconazole, paclobutrazol, pefurazoate, penconazole, prochloraz, propiconazole, prothioconazole, pyributicarb, pyrifenox, simeconazole, spiroxamine, tebuconazole, terbinafine, tetraconazole, triadimefon, triadimenol, tridemorph, triflumizole, triforine, triticonazole, uniconazole, viniconazole, voriconazole;
10) cell wall synthesis inhibitors: for example benthiavalicarb, dimethomorph, flumorph, iprovalicarb, polyoxins, polyoxorim, validamycin A;
11) melanin biosynthesis inhibitors: for example carpropamid, diclocymet, fenoxanil, phthalide, pyroquilon, tricyclazole;
12) resistance inductors: for example acibenzolar-S-methyl, probenazole, tiadinil;
13) compounds with multi-site activity: for example Bordeaux mixture, captafol, captan, chlorothalonil, copper naphthenate, copper oxide, copper oxychloride, copper preparations such as, for example, copper hydroxide, copper sulphate, dichlofluanid, dithianon, dodine, dodine free base, ferbam, fluorofolpet, folpet, guazatine, guazatine acetate, iminoctadine, iminoctadine albesilate, iminoctadine triacetate, mancopper, mancozeb, maneb, metiram, metiram zinc, oxine-copper, propineb, sulphur and sulphur preparations such as, for example, calcium polysulphide, thiram, tolylfluanid, zineb, ziram;
14) a compound selected from the following enumeration: N-methyl-(2E)-2-(2-{[6-(3-chloro-2-methylphenoxy)-5-fluoropyrimidin-4-yl]oxy}phenyl)-2-(methoxyimino)acetamide, N-methyl-(2E)-2-{2-[({[(1E)-1-(3-{[(E)-1-fluoro-2-phenylvinyl]oxy}phenyl)ethylidene]amino}oxy)methyl]phenyl}-2-(methoxyimino) acetamide, 1-(4-chlorophenyl)-2-(1H-1,2,4-triazol-1-yl) cycloheptanol, 1-[(4-methoxyphenoxy)methyl]-2,2-dimethylpropyl-1H-imidazole-1-carboxylate, 2-(4-chlorophenyl)-N-{2-[3-methoxy-4-(prop-2-yn-1-yloxy) phenyl]ethyl}-2-(prop-2-yn-1-yloxy)acetamide, 2,3,5,6-tetrachloro-4-(methylsulphonyl)pyridine, 2-butoxy-6-iodo-3-propyl-4H-chromen-4-one, 2-chloro-N-(1,1,3-trimethyl-2,3-dihydro-1H-inden-4-yl)nicotinamide, 2-phenylphenol and salts thereof, 3,4,5-trichloropyridine-2,6-dicarbonitrile, 3,4-dichloro-N-(2-cyanophenyl) isothiazole-5-carboxamide, 3-[5-(4-chlorophenyl)-2,3-dimethylisoxazolidin-3-yl]pyridine, 5-chloro-6-(2,4,6-trifluorophenyl)-N-[(1R)-1,2,2-trimethylpropyl][1,2,4] triazolo[1,5-a]pyrimidine-7-amine, 5-chloro-7-(4-methylpiperidin-1-yl)-6-(2,4,6-trifluorophenyl)[1,2,4] triazolo[1,5-a]pyrimidine, 5-chloro-N-[(1R)-1,2-dimethylpropyl]-6-(2,4,6-trifluorophenyl)[1,2,4]triazolo [1,5-a]pyrimidine-7-amine, 8-hydroxyquinoline sulphate, benthiazole, bethoxazin, capsimycin, carvone, quinomethionate, cufraneb, cyflufenamid, cymoxanil, dazomet, debacarb, dichlorophen, diclomezine, dicloran, difenzoquat, difenzoquat methylsulphate, diphenylamine, ferimzone, flumetover, fluopicolide, fluoroimide, flusulfamide, fosetyl-aluminium, fosetyl-calcium, fosetyl-sodium, hexachlorobenzene, irumamycin, methasulfocarb, methyl (2-chloro-5-{(1E)-N-[(6-methylpyridin-2-yl)methoxy] ethanimidoyl}benzyl)carbamate, methyl (2E)-2-{2-[({cyclopropyl[(4-methoxyphenyl)imino]methyl}thio)methyl] phenyl}-3-methoxyacrylate, methyl 1-(2,2-dimethyl-2,3-dihydro-1H-inden-1-yl)-1H-imidazole-5-carboxylate, methyl 3-(4-chlorophenyl)-3-{[N-(isopropoxycarbonyl) valyl]amino}propanoate, methyl isothiocyanate, metrafenone, mildiomycin, N-(3',4'-dichloro-5-fluorobiphenyl-2-yl)-3-(difluoromethyl)-1-methyl-1H-pyrazole-4-carboxamide, N-(3-ethyl-3,5,5-trimethylcyclohexyl)-3-(formylamino)-2-hydroxybenzamide, N-(4-chloro-2-nitrophenyl)-N-ethyl-4-methylbenzenesulphonamide, N-[(5-bromo-3-chloropyridin-2-yl)methyl]-2,4-dichloronicotinamide, N-[1-(5-bromo-3-chloropyridin-2-yl) ethyl]-2,4-dichloronicotin-amide, N-[1-(5-bromo-3-chloropyridin-2-yl)ethyl]-2-fluoro-4-iodonicotinamide, N-[2-(4-{[3-(4-chlorophenyl)prop-2-yn-1-yl]oxy}-3-methoxyphenyl)ethyl]-N$^2$-(methylsulphonyl)valinamide, N-{(Z)-[(cyclopropylmethoxy)imino][6-(difluoromethoxy)-2,3-difluorophenyl]methyl}-2-phenylacetamide, N-{2-[3-chloro-5-(trifluoromethyl)pyridin-2-yl] ethyl}-2-(trifluoromethyl)benzamide, natamycin, nickel dimethyl dithiocarbamate, nitrothal-isopropyl, O-{1-[(4-methoxyphenoxy)methyl]-2,2-dimethylpropyl} 1H-imidazole-1-carbothioate, octhilinone, oxamocarb, oxyfenthiin, pentachlorophenol and salts, phosphoric acid and its salts, piperalin, propamocarb fosetylate, propanosine-sodium, proquinazid, pyrrolnitrine, quintozene, tecloftalam, tecnazene, triazoxide, trichlamide, zarilamid.

Bactericides:

Bronopol, dichlorophen, nitrapyrin, nickel dimethyl dithiocarbamate, kasugamycin, octhilinone, furancarboxylic acid, oxytetracyclin, probenazole, streptomycin, tecloftalam, copper sulphate and other copper preparations.

Insecticides/Acaricides/Nematicides:

1. Acetylcholine Esterase (AChE) Inhibitors
  1.1 Carbamates (for example alanycarb, aldicarb, aldoxycarb, allyxycarb, aminocarb, azamethiphos, bendiocarb, benfuracarb, bufencarb, butacarb, butocarboxim, butoxycarboxim, carbaryl, carbofuran, carbosulfan, chloethocarb, coumaphos, cyanofenphos, cyanophos, dimetilan, ethiofencarb, fenobucarb, fenothiocarb, formetanate, furathiocarb, isoprocarb, metam-sodium, methiocarb, methomyl, metolcarb, oxamyl, pirimicarb, promecarb, propoxur, thiodicarb, thiofanox, triazamate, trimethacarb, XMC, xylylcarb)
  1.2 Organophosphates (for example acephate, azamethiphos, azinphos (-methyl, -ethyl), bromophos-ethyl, bromfenvinfos (-methyl), butathiofos, cadusafos, carbophenothion, chlorethoxyfos, chlorfenvinphos, chlormephos, chlorpyrifos (-methyl/-ethyl), coumaphos, cyanofenphos, cyanophos, chlorfenvinphos, demeton-S-methyl, demeton-S-methylsulphon, dialifos, diazinon, dichlofenthion, dichlorvos/DDVP, dicrotophos, dimethoate, dimethylvinphos, dioxabenzofos, disulfoton, EPN, ethion, ethoprophos, etrimfos, famphur, fenamiphos, fenitrothion, fensulfothion, fenthion, flupyra-zofos, fonofos, formothion, fosmethilan, fosthiazate, heptenophos, iodofenphos, iprobenfos, isazofos, isofenphos, isopropyl O-salicylate, isoxathion, malathion, mecarbam, methacrifos, methamidophos, methidathion, mevinphos, monocrotophos, naled, omethoate, oxydemeton-methyl, parathion (-methyl/-ethyl), phenthoate, phorate, phosalone, phosmet, phosphamidon, phosphocarb, phoxim, pirimiphos (-methyl/-ethyl), profenofos, propaphos, propetamphos, prothiofos, prothoate, pyraclofos, pyridaphenthion, pyridathion, quinalphos, sebufos, sulfotep, sulprofos, tebupirimfos, temephos, terbufos, tetrachlorvinphos, thiometon, triazophos, triclorfon, vamidothion)

2. Sodium channel modulators/voltage-dependent sodium channel blockers
  2.1 Pyrethroids (for example acrinathrin, allethrin (d-cis-trans, d-trans), beta-cyfluthrin, bifenthrin, bioallethrin, bioallethrin-S-cyclopentyl isomer, bioethanomethrin, biopermethrin, bioresmethrin, chlovaporthrin, cis-cypermethrin, cis-resmethrin, cis-permethrin, clocythrin, cycloprothrin, cyfluthrin, cyhalothrin, cypermethrin (alpha-, beta-, theta-, zeta-), cyphenothrin, DDT, deltamethrin, empenthrin (1R isomer), esfenvalerate, etofenprox, fenfluthrin, fenpropathrin, fenpyrithrin, fenvalerate, flubrocythrinate, flucythrinate, flufenprox, flumethrin, fluvalinate, fubfenprox, gamma-cyhalothrin, imiprothrin, kadethrin, lambda-cyhalothrin, metofluthrin, permethrin (cis-, trans-), phenothrin (1R trans-isomer), prallethrin, profluthrin, protrifenbute, pyresmethrin, resmethrin, RU 15525, silafluofen, tau-fluvalinate, tefluthrin, terallethrin, tetramethrin (1R isomer), tralomethrin, transfluthrin, ZXI 8901, pyrethrins (pyrethrum))
  2.2 Oxadiazines (for example indoxacarb)

3. Acetylcholine receptor agonists/antagonists
  3.1 Chloronicotinyls/neonicotinoids (for example acetamiprid, clothianidin, dinotefuran, imidacloprid, nitenpyram, nithiazine, thiacloprid, thiamethoxam)
  3.2 Nicotine, bensultap, cartap 4. Acetylcholine receptor modulators
  4.1 Spinosyns (for example spinosad)

5. GABA-controlled chloride channel antagonists
  5.1 Cyclodiene organochlorines (for example camphechlor, chlordane, endosulfan, gamma-HCH, HCH, heptachlor, lindane, methoxychlor)
  5.2 Fiprols (for example acetoprole, ethiprole, fipronil, vaniliprole)

6. Chloride channel activators
  6.1 Mectins (for example abamectin, avermectin, emamectin, emamectin benzoate, ivermectin, milbe-mectin, milbemycin)

7. Juvenile hormone mimetics
  (for example diofenolan, epofenonane, fenoxycarb, hydroprene, kinoprene, methoprene, pyriproxifen, triprene)

8. Ecdysone agonists/disruptors
  8.1 Diacylhydrazines (for example chromafenozide, halofenozide, methoxyfenozide, tebufenozide)

9. Chitin biosynthesis inhibitors
  9.1 Benzoylureas (for example bistrifluoron, chlofluazuron, diflubenzuron, fluazuron, flucycloxuron, flufenoxuron, hexaflumuron, lufenuron, novaluron, noviflumuron, penfluoron, teflubenzuron, tri-flumuron)
  9.2 Buprofezin
  9.3 Cyromazine 10. Inhibitors of oxidative phosphorylation, ATP disruptors
  10.1 Diafenthiuron
  10.2 Organotins (for example azocyclotin, cyhexatin, fenbutatin oxide)

11. Uncouplers of oxidative phosphorylation by interrupting the H-proton gradient
  11.1 Pyrroles (for example chlorfenapyr)
  11.2 Dinitrophenols (for example binapacyrl, dinobuton, dinocap, DNOC)

12. Site-I electron transport inhibitors
  12.1 METIs (for example fenazaquin, fenpyroximate, pyrimidifen, pyridaben, tebufenpyrad, tolfenpyrad)
  12.2 Hydramethylnone
  12.3 Dicofol 13. Site-II electron transport inhibitors
  13.1 Rotenone 14. Site-III electron transport inhibitors
  14.1 Acequinocyl, fluacrypyrim 15. Microbial disruptors of the insect gut membrane
  *Bacillus thuringiensis* strains 16. Fat synthesis inhibitors
  16.1 Tetronic acids (for example spirodiclofen, spiromesifen)
  16.2 Tetramic acids [for example 3-(2,5-dimethylphenyl)-8-methoxy-2-oxo-1-azaspiro[4.5]dec-3-en-4-yl ethyl carbonate (also known as: carbonic acid, 3-(2,5-dimethylphenyl)-8-methoxy-2-oxo-1-azaspiro[4.5]dec-3-en-4-yl ethyl ester, CAS Reg. No.: 382608-10-8) and carbonic acid, cis-3-(2,5-dimethylphenyl)-8-methoxy-2-oxo-1-azaspiro[4.5]dec-3-en-4-yl ethyl ester (CAS Reg.-No.: 203313-25-1)]

17. Carboxamides
  (for example flonicamid)

18. Octopaminergic agonists
  (for example amitraz)

19. Inhibitors of magnesium-stimulated ATPase
  (for example propargite)

20. Ryanodin receptor agonists
20.1 Benzoic dicarboxamides [for example $N^2$-[1,1-dimethyl-2-(methylsulphonyl)ethyl]-3-iodo-$N^1$-[2-methyl-4-[1,2,2,2-tetrafluoro-1-(trifluoromethyl)ethyl]phenyl]-1,2-benzenedicarboxamide (CAS Reg.-No.: 272451-65-7), flubendiamide]
20.2 Anthranilamides (for example DPX E2Y45=3-bromo-N-{4-chloro-2-methyl-6-[(methylamino)-carbonyl]phenyl}-1-(3-chloropyridin-2-yl)-1H-pyrazole-5-carboxamide)
21. Nereistoxin analogues
(for example thiocyclam hydrogen oxalate, thiosultap sodium)
22. Biologicals, hormones or pheromones
(for example azadirachtin, *Bacillus* spec., *Beauveria* spec., codlemone, *Metarrhizium* spec., *Paecilomyces* spec., *thuringiensin*, *Verticillium* spec.)
23. Active compounds with unknown or unspecific mechanisms of action
23.1 Fumigants (for example aluminium phosphide, methyl bromide, sulphuryl fluoride)
23.2 Selective antifeedants (for example cryolite, flonicamid, pymetrozine)
23.3 Mite growth inhibitors (for example clofentezine, etoxazole, hexythiazox)
23.4 Amidoflumet, benclothiaz, benzoximate, bifenazate, bromopropylate, buprofezin, quino-methionate, chlordimeform, chlorobenzilate, chloropicrin, clothiazoben, cycloprene, cyflumetofen, dicyclanil, fenoxacrim, fentrifanil, flubenzimine, flufenerim, flutenzin, gossyplure, hydramethylnone, japonilure, metoxadiazone, petroleum, piperonyl butoxide, potassium oleate, pyrafluprole, pyridalyl, pyriprole, sulfluramid, tetradifon, tetrasul, triarathene, verbutin, furthermore the compound 3-methyl-phenyl propylcarbamate (tsumacide Z), the compound 3-(5-chloro-3-pyridinyl)-8-(2,2,2-trifluoroethyl)-8-azabicyclo[3.2.1]octane-3-carbonitrile (CAS Reg. No. 185982-80-3) and the corresponding 3-endo isomer (CAS Reg. No. 185984-60-5) (cf. WO 96/37494, WO 98/25923), and preparations which contain insecticidally active plant extracts, nematodes, fungi or viruses.

The compounds (I) and (II) can be applied simultaneously, that is jointly or separately, or in succession, the sequence in the case of separate application generally not having any effect on the control results.

The active-compound combinations can be used as such, in the form of their formulations or as the use forms prepared therefrom, such as ready-to-use solutions, emulsifiable concentrates, emulsions, suspensions, wettable powders, soluble powders and granules. They are used in a customary manner, for example by watering, spraying, atomizing, broadcasting, spreading-on, and as a powder for dry seed treatment, a solution for seed treatment, a water-soluble powder for seed treatment, a water-soluble powder for slurry treatment, or by encrusting etc.

When using the active-compound combination according to the invention, the application rates can be varied within a relatively wide range, depending on the kind of application. In the treatment of parts of plants, the application rates of active-compound combination are generally between 0.1 and 10 000 g/ha, preferably between 10 and 1000 g/ha. In the treatment of seed, the application rates of active-compound combination are generally between 0.001 and 50 g per kilogram of seed, preferably between 0.01 and 10 g per kilogram of seed. In the treatment of the soil, the application rates of active-compound combination are generally between 0.1 and 10 000 g/ha, preferably between 1 and 5000 g/ha.

The good fungicidal action of the active-compound combinations according to the invention is demonstrated by the examples below. While the individual active compounds show weaknesses in their fungicidal action, the combinations show an action which exceeds a simple sum of actions.

A synergistic effect in the fungicides is always present when the fungicidal action of the active-compound combinations exceeds the total of the action of the active compounds when applied individually.

The expected activity for a given combination of active compounds can be calculated as follows, according to S. R. Colby ("Calculating Synergistic and Antagonistic Responses of Herbicide Combinations", Weeds 1967, 15, 20-22):

If
X is the efficacy when employing active compound A at an application rate of m g/ha,
Y is the efficacy when employing active compound B at an application rate of n g/ha and
E is the efficacy when employing active compounds A and B at application rates of m and n g/ha,
then $$E = X + Y - \frac{X \times Y}{100}$$

Here, the efficacy is determined in %. 0% means an efficacy which corresponds to that of the control, whereas an efficacy of 100% means that no infection is observed.

If the actual fungicidal action exceeds the calculated value, the action of the combination is superadditive, i.e. a synergistic effect is present. In this case, the actually observed efficacy must exceed the value calculated using the above formula for the expected efficacy (E).

The invention is illustrated by the examples below.

EXAMPLE 1

*Septoria tritici* Test (In Vitro)/Microtitre Plates

The microtest is carried out in microtitre plates using potato dextrose broth (PDB) as liquid test medium. The active compounds are used as technical-grade a.i., dissolved in acetone, in the case of prothioconazole and as a commercial formulation in the case of silthiofam. For inoculation, a spore suspension of *Septoria tritici* is used. After 5 days of incubation in the dark and with shaking (10 Hz), the transparency of each filled cavity of the microtitre plates is determined with the aid of a spectrophotometer.

0% means an efficacy which corresponds to the growth in the controls, whereas an efficacy of 100% means that no fungal growth is observed.

Table 1 below clearly shows that the activity found for the active-compound combinations according to the invention is greater than the one which had been calculated, i.e. that a synergistic effect is present.

TABLE 1

*Septoria tritici* test (in vitro)/microtitre plates

| Active compound | Application rate of active compound in ppm | Efficacy in % found* | calc.** |
|---|---|---|---|
| known: | | | |
| prothioconazole | 0.3 | 21 | |
| silthiofam | 0.3 | 10 | |

TABLE 1-continued

Septoria tritici test (in vitro)/microtitre plates

| Active compound | Application rate of active compound in ppm | Efficacy in % found* | Efficacy in % calc.** |
|---|---|---|---|
| mixture according to the invention: | | | |
| prothioconazole + silthiofam (1:1) | 0.3 + 0.3 | 98 | 29 |

*found = activity found
**calc. = activity calculated using Colby's formula (expected value)

EXAMPLE 2

*Pyricularia oryzae* Test (In Vitro)/Microtitre Plates

The microtest is carried out in microtitre plates using potato dextrose broth (PDB) as liquid test medium. The active compounds are used as technical-grade a.i., dissolved in acetone, in the case of prothioconazole and as a commercial formulation in the case of silthiofam. For inoculation, a spore suspension of *Pyricularia oryzae* is used. After 5 days of incubation in the dark and with shaking (10 Hz), the transparency of each filled cavity of the microtitre plates is determined with the aid of a spectrophotometer.

0% means an efficacy which corresponds to the growth in the controls, whereas an efficacy of 100% means that no fungal growth is observed.

Table 2 below clearly shows that the activity found for the active-compound combinations according to the invention is greater than the one which had been calculated, i.e. that a synergistic effect is present.

TABLE 2

*Pyricularia oryzae* test (in vitro)/microtitre plates

| Active compound | Application rate of active compound in ppm | Efficacy in % found* | Efficacy in % calc.** |
|---|---|---|---|
| known: | | | |
| prothioconazole | 3 | 23 | |
| silthiofam | 3 | 29 | |
| mixture according to the invention: | | | |
| prothioconazole + silthiofam (1:1) | 3 + 3 | 95 | 45 |

*found = activity found
**calc. = activity calculated using Colby's formula (expected value)

The invention claimed is:

1. An active-compound combination, comprising a compound of the formula (I)

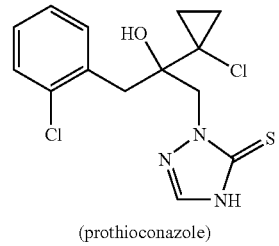

(prothioconazole)

and the compound of the formula (II)

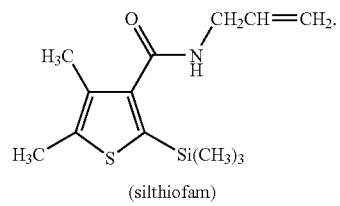

(silthiofam)

2. An active-compound combination to claim 1, wherein the weight ratio of the active compound of the formula (I) to the active compound of the formula (II) is from 1:0.02 to 1:20.

3. An active-compound combination according to claim 1, further comprising one or more fungicidally or insecticidally active compounds.

4. A method for controlling phytopathogenic fungi, comprising contacting said fungi or their habitat with an active-compound combination according to claim 1.

5. A method of protecting plants or treating seeds comprising contacting said plants or said seeds with an active-compound combination according to claim 1.

6. The method according to claim 5, where said seeds are seeds of transgenic plants.

7. A fungicidal composition, comprising an active-compound combination according to claim 1, and extenders, surfactants or combinations thereof.

8. A process for preparing fungicidal compositions comprising mixing the active compounds of claim 1 with extenders, surfactants or combinations thereof.

9. A seed coated with an active-compound combination according to claim 1.

10. A seed of trangenic plants coated with an active-compound combination according to claim 1.

* * * * *